United States Patent [19]

Niwa et al.

[11] Patent Number: 4,938,227
[45] Date of Patent: Jul. 3, 1990

[54] METHOD AND APPARATUS FOR MEASURING BLOOD PRESSURE

[75] Inventors: Minoru Niwa, Nagoya; Hifumi Yokoe, Kosai, both of Japan

[73] Assignee: Colin Electronics Co., Ltd., Aichi, Japan

[21] Appl. No.: 310,893

[22] Filed: Feb. 16, 1989

[51] Int. Cl.⁵ .......................................... A61B 5/0225
[52] U.S. Cl. ...................................... 128/682; 128/680
[58] Field of Search ......................... 128/672, 677–686

[56] References Cited

U.S. PATENT DOCUMENTS

| | | | |
|---|---|---|---|
| 3,450,131 | 6/1969 | Vogt | 128/682 |
| 3,814,083 | 6/1974 | Fletcher et al. | 128/683 |
| 3,930,494 | 1/1976 | Maurer et al. | 128/682 |
| 4,180,061 | 12/1979 | Kamimura et al. | 128/681 |
| 4,328,810 | 5/1982 | Hill et al. | 128/682 X |
| 4,475,557 | 10/1984 | Hatscher et al. | 128/681 |
| 4,501,281 | 2/1985 | Furukawa | 128/677 X |
| 4,635,645 | 1/1987 | Fukushima | 128/680 |

*Primary Examiner*—Angela D. Sykes
*Attorney, Agent, or Firm*—Oliff & Berridge

[57] ABSTRACT

A method and apparatus for measuring blood pressure of a subject based on Korotkoff sounds which are produced synchronously with heartbeat of the subject by pressing a body portion of the subject. The method including the steps of detecting the Korotkoff sounds by a microphone, the microphone generating electric signal corresponding to the detected Korotkoff sounds in a whole frequency range thereof; separating from the electric signal a signal component corresponding to the Korotkoff sounds in a comparatively high frequency range out of the whole frequency range; measuring, regarding the signal component, time of occurrence of at least one Korotkoff sound in the comparatively high frequency range; determining at least one time window regarding the electric signal, based on the time of occurrence measured regarding the signal component, the at least one time window consisting of a time interval smaller than a time period of occurrence of the Korotkoff sounds; and collecting a Korotkoff sound occurring in the time interval of each of the at least one time window determined regarding the electric signal, the collected Korotkoff sound being utilized for determining the blood pressure of the subject.

18 Claims, 4 Drawing Sheets

METHOD AND APPARATUS FOR MEASURING BLOOD PRESSURE

BACKGROUND OF THE INVENTION

1. Field of the Invention

The present invention relates to improvements in a method and apparatus for measuring blood pressure by detecting Korotkoff sounds.

2. Discussion of the Prior Art

There has been known the technique of detecting with a microphone Korotkoff sounds which are produced from a living body synchronously with heartbeat of the body by pressing a portion of the body, and determining blood pressure based on the detected Korotkoff sounds. Recently this technique is used for continuously and regularly measuring blood pressure of a subject while the subject is doing physical exercise.

In the case of measuring blood pressure of a subject who is doing physical exercise by the technique in question, however, the detected Korotkoff sounds tend to include noise resulting from the exercise. In other words, a frequency range of the Korotkoff sounds overlaps that of such noise. Thus, accuracy of the blood pressure measurement has been unsatisfactory. The noise includes sounds produced by friction or rubbing of an inflatable cuff and sounds produced by striking or collision of hands, feet and other body members, both of which are comparatively large and therefore troublesome, namely, tend to be detected by the microphone together with Korotkoff sounds. Thus, the detected Korotokoff sounds are not satisfactory to be used for blood pressure measurement.

SUMMARY OF THE INVENTION

The inventors have conducted a series of studies and researches about blood pressure measurement based on Korotkoff sounds, and found that noise resulting from physical exercise of a subject has substantially no frequency component corresponding to the Korotkoff sounds in a comparatively high frequency range thereof. Specifically, the noise caused by friction of an inflatable cuff has a frequency range higher than a whole frequency range of the Korotkoff sounds. Further, since the noise caused by collision of hands and feet of a subject is conducted through the body of the subject, the noise has a frequency range corresponding to a comparatively low frequency range of the Korotkoff sounds. The present invention has been achieved based on this finding.

It is therefore an object of the present invention to provide a method and apparatus for accurately measuring blood pressure by detecting Korotkoff sounds, wherein the Korotkoff sounds are clearly separated from noise mixed therewith when the Korotkoff sounds are detected.

According to a first aspect of the present invention, there is provided a method of measuring blood pressure of a subject based on Korotkoff sounds which are produced synchronously with heartbeat of the subject by pressing a body portion of the subject, the method comprising the steps of: (a) detecting the Korotkoff sounds by a microphone, the microphone generating electric signal corresponding to the detected Korotkoff sounds in a whole frequency range thereof, (b) separating from the electric signal a signal component corresponding to the Korotkoff sounds in a comparatively high frequency range out of the whole frequency range, (c) measuring, regarding the signal component, time of occurrence of a Korotkoff sound in the comparatively high frequency range, (d) determining at least one time window regarding the electric signal, based on the time of occurrence measured regarding the signal component, the at least one time window consisting of a time interval smaller than a time period of occurrence of the Korotkoff sounds, and (e) collecting a Korotkoff sound occurring in the time interval of each of the at least one time window determined regarding the electric signal, the collected Korotkoff sound being utilized for determining the blood pressure of the subject.

In the blood pressure measuring method arranged as described above, the Korotkoff sounds in the comparatively high frequency range are separated from the whole frequency range of the Korotkoff sounds, and at least one time window is determined regarding the Korotkoff sounds in the whole frequency range, based on the time of occurrence of a Korotkoff sound in the comparatively high frequency range. The at least one time window consists of a time interval shorter than a time period of occurrence of the Korotkoff sounds. The Korotkoff sound occurring in the time interval of each of the at least one time window is collected, and the collected Korotkoff sound is utilized for determining the blood pressure. Since the Korotkoff sounds in the comparatively high frequency range thereof are free from influence of noise produced from physical exercise of a subject, as previously described, the Korotkoff sounds in the whole frequency range thereof are clearly separated from the noise as a result of being selected through the time window(s) determined based on the time of occurrence of a high-frequency Korotkoff sound. The instant method allows accurate blood pressure measurement, even in the case where the detected Korotkoff sounds are mixed regarding frequency with noise resulting from physical exercise of a subject. Thus, the present method has overcome the problem that, when Korotkoff sounds are detected with a microphone, the detected Korotkoff sounds are mixed with noise whose frequency overlaps that of the Korotkoff sounds.

In a preferred embodiment of the method of the present invention, the comparatively high frequency range of the Korotkoff sounds ranges from 40 to 80 Hz. Alternatively, the range may range from 40 to 50 Hz, or may range from 50 to 80 Hz.

In another embodiment of the method of the present invention, the time interval of the at least one time window falls in the range of 200 to 300 ms.

According to a feature of the present invention, the invention further comprises the step of separating from the electric signal another signal component corresponding to the Korotkoff sounds in a comparatively low frequency range out of the whole frequency range, the at least one time window being determined regarding the another signal component. In this case, it is preferred that the comparatively low frequency range of the Korotkoff sounds range from 20 to 50 Hz.

In yet another embodiment of the method of the present invention, the step of detecting the Korotkoff sounds by the microphone is effected as the pressing force to press the body portion of the subject is decreased. Alternatively, this step may be effected as the pressing force to press the body portion of the subject is increased.

According to a second aspect of the present invention, there is provided a blood pressure measuring apparatus for automatically measuring blood pressure of a subject based on Korotkoff sounds which are produced synchronously with heartbeat of the subject by pressing a body portion of the subject, the apparatus comprising (1) a microphone for detecting the Korotkoff sounds, the microphone generating electric signal corresponding to the detected Korotkoff sounds in a whole frequency range thereof; (2) filter means for separating from the electric signal a signal component corresponding to the Korotkoff sounds in a comparatively high frequency range out of the whole frequency range; (3) measuring means for measuring, regarding the signal component, time of occurrence of a Korotkoff sound in the comparatively high frequency range; (4) gate means for determining at least one time window regarding the electric signal, based on the time of occurrence measured regarding the signal component, the at least one time window consisting of a time interval smaller than a time period of occurrence of the Korotkoff sounds, the gate means collecting a Korotkoff sound occurring in the time interval of each of the at least one time window; and (5) determining means for determining the blood pressure of the subject based on the collected Korotkoff sound.

In the blood pressure measuring apparatus constructed as described above, Korotkoff sounds in a whole frequency range thereof are detected by the microphone, and a signal component representing a Korotkoff sound in the comparatively high frequency range thereof is separated by the filter means from electric signal supplied from the microphone which signal represents not only the Korotkoff sounds in the whole frequency range thereof but also noise resulting from physical exercise of a subject. The gate means determines at least one time window regarding the electric signal, based on the time of occurrence of the Korotkoff sound in the comparatively high frequency range. The at least one time window consists of a time interval smaller than a time period of occurrence of Korotkoff sounds. Thus, the Korotkoff sound occurring in the time interval of each of the at least one time window is collected. The thus collected Korotkoff sound(s) is/are utilized to determine blood pressure. As described above, the Korotkoff sounds in the comparatively high frequency range are free from noise produced from a subject who is doing physical exercise. Accordingly, the Korotkoff sound(s) collected through the time window(s), which is/are determined regarding the electric signal based on the time of occurrence of a high-frequency Korotkoff sound, is clearly separated from the noise. As a result, the instant apparatus is capable of measuring blood pressure with accuracy even if the detected Korotkoff sounds are mixed with noise whose frequency range overlaps that of the Korotkoff sounds.

In a preferred embodiment of the apparatus of the present invention, the filter means comprises a band-pass filter transmitting the signal component corresponding to the comparatively high frequency range from 40 to 80 Hz. Alternatively, the filter means may comprise a band-pass filter transmitting the signal component correponding to the comparatively high frequency range from 40 to 50 Hz or from 50 to 80 Hz.

In another embodiment of the apparatus of the inveniton, the gate means determines the at least one time window consisting of a time interval of 200 to 300 ms.

According to a feature of the present invention, the apparatus further comprises another filter means for separating, from the electric signal, another signal component corresponding to the Korotkoff sounds in a comparatively low frequency range out of the whole frequency range, the gate means determining the at least one time window regarding the another signal component. In this case, it is preferred that the another filter means comprise a band-pass filter transmitting the another signal component corresponding to the comparatively low frequency range from 20 to 50 Hz.

In yet another embodiment of the apparatus of the invention, the microphone detects the Korotkoff sounds as the pressing force to press the body portion of the subject is decreased. AlternativelY, the microphone may detect the Korotkoff sounds as the pressing force to press the body portion of the subject is increased.

BRIEF DESCRIPTION OF THE DRAWINGS

The above and optional objects, features and advantages of the present invention will be better understood by reading the following detailed description of the presently preferred embodiment of the invention, when considered in connection with the accompanying drawings, in which.

DETAILED DESCRIPTION OF THE PREFERRED EMBODIMENT

Figure 1:
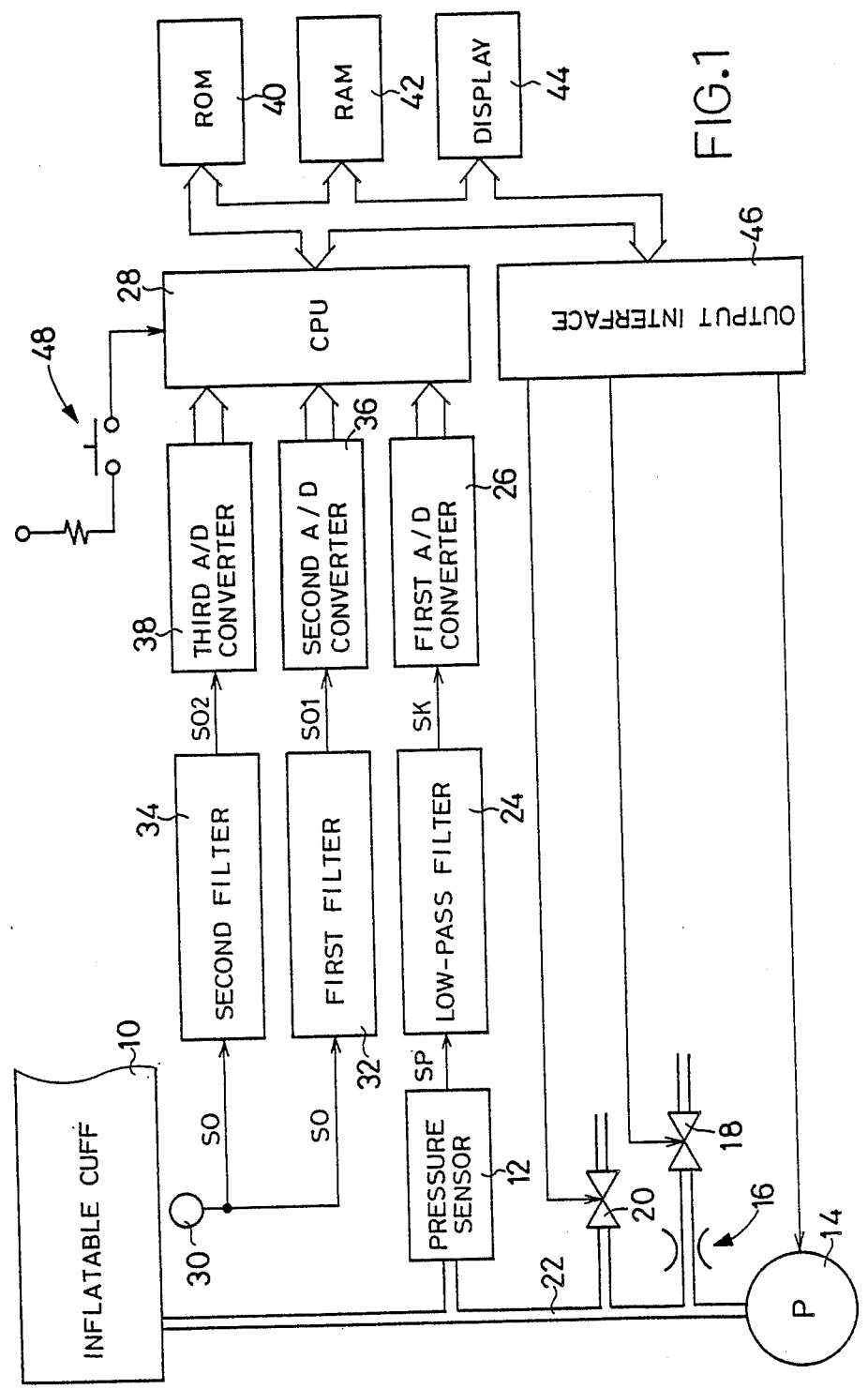
FIG. 1 is a diagrammatic view of a control circuit of a blood pressure measuring apparatus of the present invention.

Referring first to FIG. 1, there is shown a control circuit of a blood pressure measuring apparatus of the present invention. In the figure, reference numeral 10 designates a bag-like rubber inflatable cuff to be set around an upper arm or the like of a subject. The cuff 10 is connected via piping 22 to a pressure sensor 12, an air pump 14, a slow-deflation restrictor 16, a slow-deflation electromagnetic valve 18, and a rapid-deflation electromagnetic valve 20. The pressure sensor 12 generates pressure signal SP representing pressure variation in the bag of the inflatable cuff 10, to a low-pass filter 24. The low-pass filter 24 separates from pressure signal SP cuff-pressure signal SK representing cuff pressure (static pressure) P in the cuff 10, and supplies signal SK to a CPU (central processing unit) 28 via a first A/D (analog-to-digital) converter 26.

A microphone 30 is set near the cuff 10 on the upper arm of the subject. The microphone 30 detects Korotkoff sounds that are pulse sounds produced from the subject as a result of pressing the upper arm by the inflated cuff 10, and generates Korotkoff-sound signal SO to a first band-pass filter 32 (hereinafter, referred to as the first filter) and a second band-pass filter 34 (hereinafter, referred to as the second filter). The first filter 32 separates, from signal SO, signal SO1 (a first signal component) corresponding to a frequency range of 20 to 50 Hz, while the second filter 34 separates, from signal SO, signal SO2 (a second signal component) corresponding to a frequency range of 40 to 80 Hz. The frequency range of 20–50 Hz corresponds to a comparatively low frequency range of Korotkoff sounds, while the frequency range of 40–80 Hz corresponds to a comparatively high frequency range of Korotkoff sounds. Signals SO1 and SO2 are supplied to the CPU 28 via a second and a third A/D converter 36, 38, respectively. The second filter 34 serves as the filter means for separating, from electric signal SO supplied from the microphone, the signal component corresponding to the Korotkoff sounds in the comparatively high frequency range thereof.

The CPU 28 is coupled via data bus 39 to a ROM (read only memory) 40, a RAM (random access memory) 42, a display 44, and an output interface 46, and processes the received signals according to programs pre-stored in the ROM 40 and by utilizing temporary-storage function of the RAM 42. While the CPU 28 controls the operation of each of the air pump 14 and electromagnetic valves 18, 20, the CPU 28 effects operations for blood pressure measurement. Specifically, the CPU 28 determines blood pressure based on signals SO1, SO2 supplied from the first and second filters 32, 34, and commands the display 44 to display the determined blood pressure.

Figure 2:
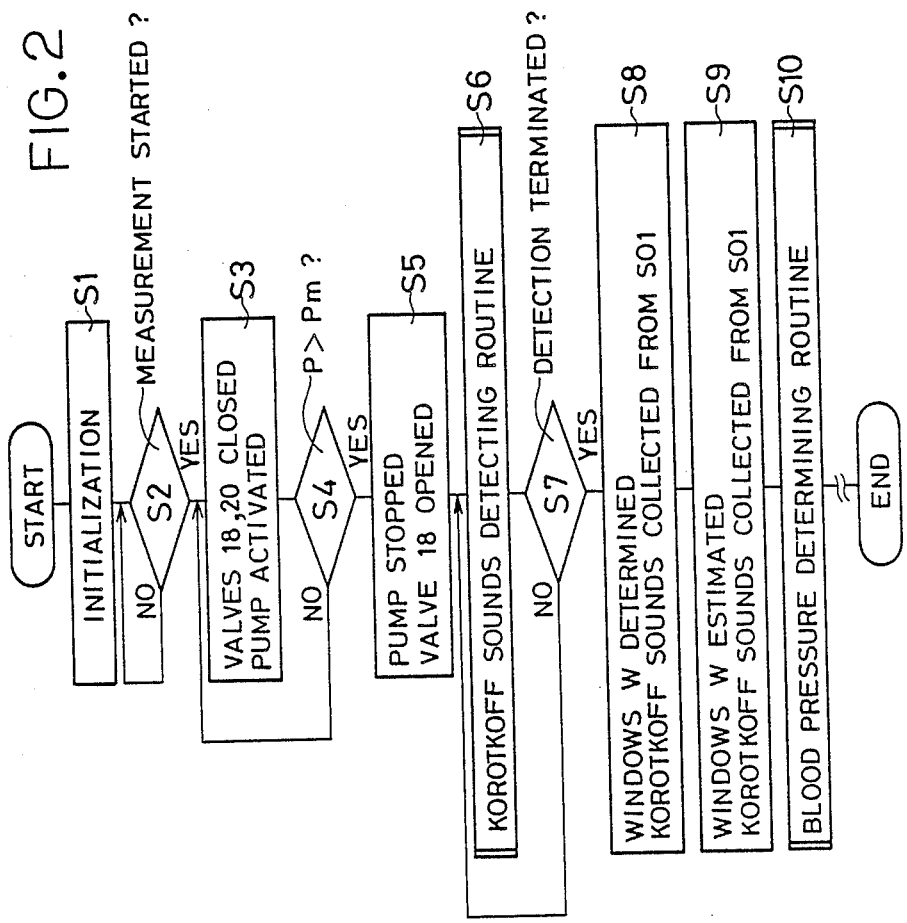
FIG. 2 is a flow chart illustrating operation of the apparatus of FIG. 1.
Figure 3:
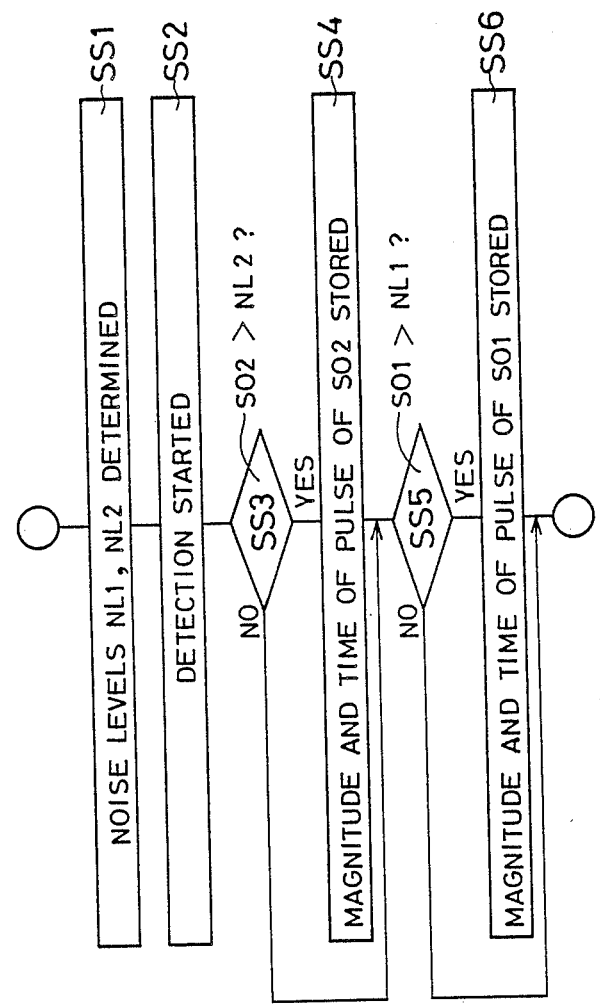
FIG. 3 is a flow chart illustrating a Korotkoff sounds detecting routine in the flow chart of FIG. 2.

Referring next to FIGS. 2 and 3, there are shown the flow charts according to which the instant apparatus is operated.

Upon application of electric power to the apparatus, the control of the CPU 28 goes to step S1 (FIG. 2) at which initialization of the apparatus is effected. Step S1 is followed by step S2 at which it is judged whether or not a START pushbutton switch 48 (FIG. 1) has been pushed, namely, whether or not blood pressure measurement has been started. If the judgement at step S2 is negative (NO), step S2 is repeated until the judgement is turned to be affirmative (YES). Once the judgement at step S2 is affirmative, step S2 is followed by step S3 at which both the electromagnetic valves 18, 20 are closed and the air pump 14 is activated. At the following step S4 it is judged whether or not cuff pressure P has exceeded a predetermined target level Pm. This target pressure Pm is predetermined to be sufficiently higher than maximum blood pressure of normal people, for example about 180 mmHg. If cuff pressure P has not reached the target level Pm and accordingly the judgement at step S4 is negative, steps S3 and S4 are repeated until the judgement at step S4 is turned to be affirmative. Meanwhile, if cuff pressure P has exceeded the target level Pm, step S4 is followed by step S5 at which the air pump 14 is stopped and the electromagnetic valve 18 is opened, so as to slowly deflate the cuff 10, namely, slowly decrease cuff pressure P in the cuff 10. At the following step S6 the CPU 28 effects a Korotkoff sounds detecting subroutine as indicated by the flow chart of FIG. 3.

In this subroutine, at step SS1 the CPU 28 determines noise level NL1 regarding signal SO1 (or the first filter 32 coupled to the CPU 28 via the second A/D converter 36) and noise level NL2 regarding signal SO2 (the second filter 34 coupled to the CPU 28 via the third A/D converter 38), under the condition that Korotkoff sounds are not produced from the subject. Noise levels NL1, NL2 serve as reference values for detecting pulses representing Korotkoff sounds, from signals SO1, SO2, respectively. Step SS1 is followed by step SS2 at which the CPU 28 is made ready to read in pulses of Korotkoff sounds from signals SO1, SO2. At the following step SS3 it is judged whether or not a magnitude of a pluse of signal SO2 from the second filter 34 has exceeded noise level NL2. If the judgement at step SS3 is negative, namely, if the magnitude of signal SO2 has not reached noise level NL2, the control of the CPU 28 skips the following step SS4 and advances to step SS5. On the other hand, if the judgement at step SS3 is affirmative, step SS3 is followed by step SS4 at which the CPU 28 stores in the RAM 42 the pulse (of signal SO2) whose magnitude has exceeded noise level NL2, together with time of occurrence of the pulse, as illustrated in a lower portion of the graph of FIG. 4. At step SS5 it is judged whether or not a magnitude of a pulse of signal SO1 has exceeded noise level NL1. If the judgement at step SS5 is negative, namely, if the magnitude of signal SO1 has not reached noise level NL1, the control of the CPU 28 skips the following step SS6 and goes to step S7 of the main routine (FIG. 2). On the other hand, if the judgement at step SS5 is affirmative, step SS5 is followed by step SS6 at which the CPU 28 stores the pulse (of signal SO1) whose magnitude has exceeded noise level NL1, together with time of occurrence of the pulse, as illustrated in an upper portion of the graph of FIG. 4. Subsequently the control of the CPU 28 returns to the main routine.

Figure 4:
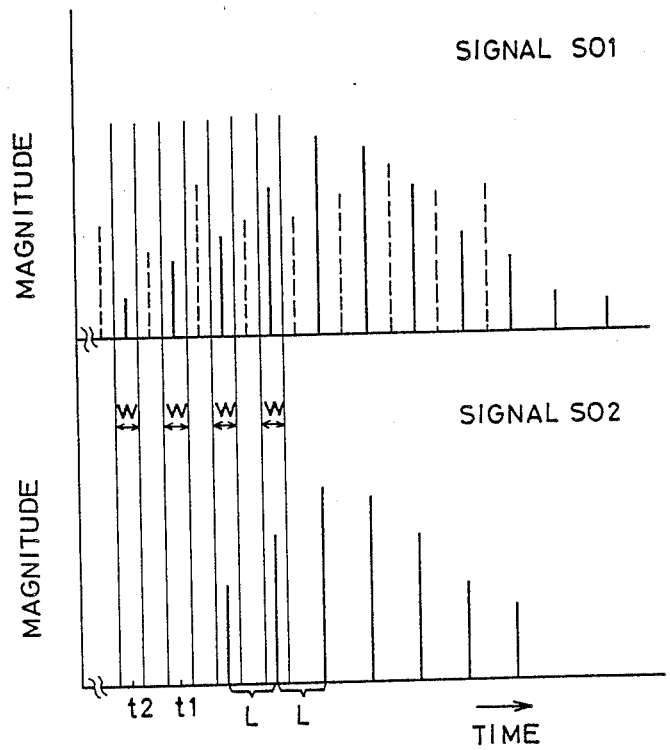
FIG. 4 is a graph showing the Korotkoff sounds in a comparatively low frequency range and the Korotkoff sounds in a comparatively high frequency range, both of which are detected at the Korotkoff sounds detecting routine of FIG. 3.

At step S7 it is judged whether or not detection of pulses representing Korotkoff sounds has been terminated at a current detecting cycle. This judgement is made based on, for example, whether or not cuff pressure P has been decreased below pressure level 30 mmHg which pressure is predetermined to be sufficiently lower than minimum blood pressure of normal people. If the judgement at step S7 is negative, step S6 (Korotkoff sounds detecting routine) is repeated until the termination of detection of the Korotkoff sounds at the current detecting cycle. Thus, pulses of signal SO2 and pulses of signal SO1 are consecutively detected as cuff pressure P is slowly decreased, and stored in the RAM 42 as indicated in the graph of FIG. 4. In the graph, solid lines indicate pulses of signals SO1, SO2, while broken lines indicate noise detected by the microphone 30 and transmitted to the CPU 28 through the first and second filters 32, 34.

If the judgement at step S7 is affirmative, namely, if the detection of Korotkoff sounds at the current detecting cycle has been terminated, step S7 is followed by step S8 at which the CPU 28 determines a time window W consisting of a time interval, regarding each of the pulses of signal SO2, such that the time of occurrence of each pulse is positioned at the center of the corresponding time window W. As illustrated in the upper portion of the graph of FIG. 4, a pulse occurring in the time interval of each of time windows which are determined regarding signal SO1 so as to correspond to the time windows W determined regarding signal SO2, is collected and transferred to another graph (not shown) in the RAM 42.

At the following step S9 the CPU 28 estimates times of occurrence of pulses of signal SO2 as indicated at t1, t2, . . . in the lower portion of the graph of FIG. 4, based on a time interval L between each pair of the detected consecutive pulses of signal SO2, namely, a time period of heartbeart of the subject. Alternatively, the times t1, t2, . . . may be estimated based on heartbeat period of normal people. While in the graph of FIG. 4 the estimated times t1, t2, . . . are indicated on the systolic-pressure side, times of occurrence of pulses are similarly estimated on the diastolic-pressure side. Similar to the actually detected pulses, a time window W is determined regarding the estimated pulses such that each of the estimated times t1, t2, ... is positioned at the center of the corresponding time window W. A pulse occurring in each of time windows which are determined regarding signal SO1 so as to correspond to the time windows W determined regarding the estimated pulses of signal SO2, is collected and transferred to the above-indicated another graph in the RAM 42. The time interval of each of the time windows W is predetermined to be sufficiently shorter than the above-indicated time interval L, for example it falls within the range of 200 to 300 ms. Step S9 is provided because generally the detected pulses of signal SO2 do not have any clear pulses in the diastolic-pressure region as indicated at the right-hand end portion of the graph of FIG. 4.

Thus, clear data about the Korotkoff sounds in the whole frequency range thereof are collected in the above-indicated another graph, as if only the noise were removed from the upper graph of FIG. 4. Step S9 is followed by step S10 at which the CPU 28 effects a blood pressure determining routine consisting of an algorithm well-known for measuring blood pressure by detecting Korotkoff sounds. The CPU 28 determines maximum and minimum blood pressure based on the clear data about the Korotkoff sounds obtained at step S9. In the present embodiment, step S8 stored in the form of program in the ROM 40 and the CPU 28 and RAM 42 for effecting step S8, serve as the means for measuring the time of occurrence of a high-frequency Korotkoff sound. Further, step S9 and the CPU 28 and RAM 42 for effecting step S9 serve as the gate means for determining at least one time window (W) regarding the electric signal (SO1) supplied from the microphone 30, and collecting a Korotkoff sound occurring in the at least one time window. Meanwhile, step S10 and the CPU 28 and RAM 42 for effecting step S10 serve as the means for determining blood pressure. The determined blood pressure is displayed on the display 44, and the electromagnetic valve 20 is opened to rapidly deflate the cuff 10.

In the illustrated embodiment, electric signal SO detected by the microphone 30 which signal corresponds to the Korotkoff sounds in the whole frequency range thereof, is separated into signal SO1 corresponding to the Korotkoff sounds in the comparatively low frequency range through the first filter 32, and signal SO2 corresponding to the Korotkoff sounds in the comparatively high frequency range through the second filter 34. However, it is possible to utilize signal SO in place of signal SO1. Further, although in the illustrated embodiment the frequency ranges of signal SO1 (20–50 Hz) and signal SO2 (40–80 Hz) overlap each other, it is possible to utilize signals SO1, SO2 whose frequency ranges are apart from each other, for example signal SO2 ranging from 50 to 80 Hz and signal SO1 ranging from 20 to 50 Hz. Furthermore, it is possible to utilize signal SO2 whose frequency ranges from 40 to 50 Hz and signal SO1 whose frequency ranges from 20 to 50 Hz. In the latter case, the frequency range of signal SO2 completely overlaps that of signal SO1.

Signal SO2 corresponding to the Korotkoff sounds in the comparatively high frequency range thereof, is free from noise resulting from physical exercise of a subject, as shown in the lower portion of the graph of FIG. 4. Accordingly, in the present blood pressure measuring method and apparatus, time of occurrence of a pulse of signal SO2 is utilized as a reference time for estimating times of occurrence of pulses regarding signal SO2, and determining a time window regarding each of the pulses of signal SO1 which correspond to the detected and estimated pulses of signal SO2. Since the time windows are sufficiently shorter than the time period of heartbeat of the subject, only the Korotkoff sounds are clearly separated from signal SO1 including the noise mixed with the Korotkoff sounds, as a result of being collected through the time windows. Thus, the instant method and apparatus are capable of more accurate blood pressure measurement than conventional methods and apparatus.

While in the illustrated embodiment the time widows W are determined based on the pulses of signal SO2 after all the pulses of signals SO1 and SO2 have been detected and the Korotkoff sounds are collected from signal SO1 through the time windows W, it is possible to determine a time window regarding signal SO1 each time a pulse of signal SO2 is detected and collect a Korotkoff sound through the determined time window.

Although in the illustrated embodiment the blood pressure measurement is effected as pressure P in the cuff 10 is decreased, it is possible to measure blood pressure as the cuff pressure is increased.

While the present invention has been described in its presently preferred embodiment with detailed particularities, it is to be understood that the invention may be embodied with various changes, improvements and modifications that may occur to those skilled in the art without departing from the spirit and scope of the invention defined in the appended claims.

What is claimed is:

1. A method of measuring a blood pressure of a subject based on Korotkoff sounds which are produced synchronously with heartbeat of the subject by pressing a body portion of the subject, the method comprising the steps of:

detecting said Korotkoff sounds by a microphone, said microphone generating electric signals corresponding to the detected Korotkoff sounds in a whole frequency range thereof, separating from at least one of said electric signals a signal component corresponding to a Korotkoff sound in a comparatively high frequency range out of said whole frequency range, measuring, regarding said signal component, a time of occurrence of said Korotkoff sound in said comparatively high frequency range, determining at least one time window regarding said electric signals, based on said time of occurrence measured regarding said signal component, said at least one time window consisting of a time interval smaller than a time period of occurrence of said Korotkoff sounds, and collecting a Korotkoff sound occurring in the time interval of each of said at least one time window determined regarding said electric signals, the collected Korotkoff sound being utilized for determining the blood pressure of the subject.

2. The method as set forth in claim 1, wherein said comparatively high frequency range of said Korotkoff sounds ranges from 40 to 80 Hz.

3. The method as set forth in claim 1, wherein said comparatively high frequency range of said Korotkoff sounds ranges from 40 to 50 Hz.

4. The method as set forth in claim 1, wherein said comparatively high frequency range of said Korotkoff sounds ranges from 50 to 80 Hz.

5. The method as set forth in claim 1, wherein the time interval of said at least one time window falls in the range of 200 to 300 ms.

6. The method as set forth in claim 1, further comprising the step of
separating from said at least one electric signal another signal component corresponding to a Korotkoff sound in a comparatively low frequency range out of said whole frequency range,
storing said another signal component, said at least one time window being determined regarding said stored another signal component.

7. The method as set forth in claim 6, wherein said comparatively low frequency range of said Korotkoff sounds ranges from 20 to 50 Hz.

8. The method as set forth in claim 1, wherein the step of detecting said Korotkoff sounds by said microphone is effected as the pressing force to press said body portion of the subject is decreased.

9. The method as set forth in claim 1, wherein the step of detecting said Korotkoff sounds by said microphone is effected as the pressure force to press said body portion of the subject is increased.

10. A blood pressure measuring apparatus for automatically measuring a blood pressure of a subject based on Korotkoff sounds which are produced synchronously with the heartbeat of the subject by pressing a body portion of the subject, the apparatus comprising:
a microphone for detecting said Korotkoff sounds, said microphone generating electric signals corresponding to the detected Korotkoff sounds in a whole frequency range thereof;
filter means for separating from at least one of said electric signals a signal component corresponding to a Korotkoff sound in a comparatively high frequency range out of said whole frequency range;
measuring means for measuring, regarding said signal component, a time of occurrence of said Korotkoff sound in said comparatively high frequency range;
gate means for determining at least one time window regarding said electric signals, based on said time of occurrence measured regarding said signal component, said at least one time window consisting of a time interval smaller than a time period of occurrence of said Korotkoff sounds, said gate means collecting a Korotkoff sound occurring in the time interval of each of said at least one time window; and
determining means for determining the blood pressure of the subject based on said Korotkoff sounds including the collected Korotkoff sound.

11. The apparatus as set forth in claim 10, wherein said filter means comprises a band-pass filter transmitting said signal component corresponding to said comparatively high frequency range from 40 to 80 Hz.

12. The apparatus as set forth in claim 10, wherein said filter means comprises a band-pass filter transmitting said signal component correponding to said comparatively high frequency range from 40 to 50 Hz.

13. The apparatus as set forth in claim 10, wherein said filter means comprises a band-pass filter transmitting said signal component corresponding to said comparatively high frequency range from 50 to 80 Hz.

14. The apparatus as set forth in claim 10, wherein said gate means determines said at least one time window consisting of a time interval of 200 to 300 ms.

15. The apparatus as set forth in claim 10, further comprising:
another filter means for separating from said at least one electric signal another signal component corresponding to a Korotkoff sound in a comparatively low frequency range out of said whole frequency range, and
storing means for storing said another signal component,
said gate means determining said at least one time window regarding said stored another signal component.

16. The apparatus as set forth in claim 15, wherein said another filter means comprises a band-pass filter transmitting said another signal component corresponding to said comparatively low frequency range from 20 to 50 Hz.

17. The apparatus as set forth in claim 10, wherein said microphone detects said Korotkoff sounds as the pressing force to press said body portion of the subject is decreased.

18. The apparatus as set forth in claim 10, wherein said microphone detects said Korotkoff sounds as the pressing force to press said body portion of the subject is increased.

* * * * *